US00PP33286P2

(12) United States Plant Patent
Wood

(10) Patent No.: US PP33,286 P2
(45) Date of Patent: Jul. 27, 2021

(54) ***THUJA* PLANT NAMED 'SMNTDGT'**

(50) Latin Name: *Thuja occidentalis*
Varietal Denomination: SMNTDGT

(71) Applicant: Spring Meadow Nursery, Inc., Grand Haven, MI (US)

(72) Inventor: Timothy D Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/115,138

(22) Filed: Dec. 8, 2020

(51) Int. Cl.
*A01H 5/12* (2018.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00; A01H 5/12
See application file for complete search history.

*Primary Examiner* — Kent L Bell
(74) *Attorney, Agent, or Firm* — Cassandra Bright

(57) ABSTRACT

A new and distinct variety of *Thuja* plant named 'SMNTDGT' is disclosed, characterized by a short plant habit and dense foliage. Plants have distinctive dense ovate plant habit without pinching or pruning, making plants low maintenance. The new cultivar is a *Thuja*, suitable for ornamental garden purposes.

2 Drawing Sheets

Latin name of the genus and species: *Thuja occidentalis*.
Variety denomination: 'SMNTDGT'.

BACKGROUND OF THE INVENTION

The new cultivar, hereinafter referred to as 'SMNTDGT', was discovered by the inventor, Timothy Wood, in a commercial nursery in Grand Haven, Mich. This new discovery is the result of an open-pollination of the seed parent *Thuja occidentalis* 'Wareana'(unpatented) with unidentified pollen parents conducted during 2001.

The new variety was first identified as an interesting new plant during 2004 at the same commercial nursery in Grand Haven, Mich. After identifying the new variety as a potentially interesting selection, the inventor first organized propagation of 'SMNTDGT' by softwood cuttings at the same commercial nursery during 2004. The inventor continued controlled testing and propagation, assessing stability of the unique characteristics of this variety. At least sixteen generations have been asexually reproduced and have shown that the unique features of this cultivar are stable and reproduced true to type.

SUMMARY OF THE INVENTION

The cultivar 'SMNTDGT' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNTDGT'. These characteristics in combination distinguish 'SMNTDGT' as a new and distinct *Thuja* cultivar:

1. Short plant habit.
2. Dense foliage.
3. Good container plant, pinching not required.

4. Unique dense ovate plant habit.
5. Low maintenance plant, with an attractive shape without pruning.

COMPARISON TO PARENT VARIETY

'SMNTDGT' is similar in most horticultural characteristics to the parent variety *Thuja occidentalis* 'Wareana'. Plants of the new cultivar 'SMNTDGT' however, differ in the following:

1. The new variety is more vigorous and full than the seed parent, which is less vigorous and produces less branches.
2. The new variety has lighter green foliage than the seed parent.

COMMERCIAL COMPARISON

*Thuja* 'SMNTDGT' can be compared to the commercial variety *Thuja* 'Smaragd', unpatented. Plants are similar in most horticultural characteristics, however, plants of the new variety differ in the following:

1. 'SMNTDGT' has lighter green foliage than this comparator.
2. 'SMNTDGT' has a ovate plant habit, this comparator has a pyramidal habit.

BRIEF DESCRIPTION OF THE PHOTOGRAPHS

Figure 1:
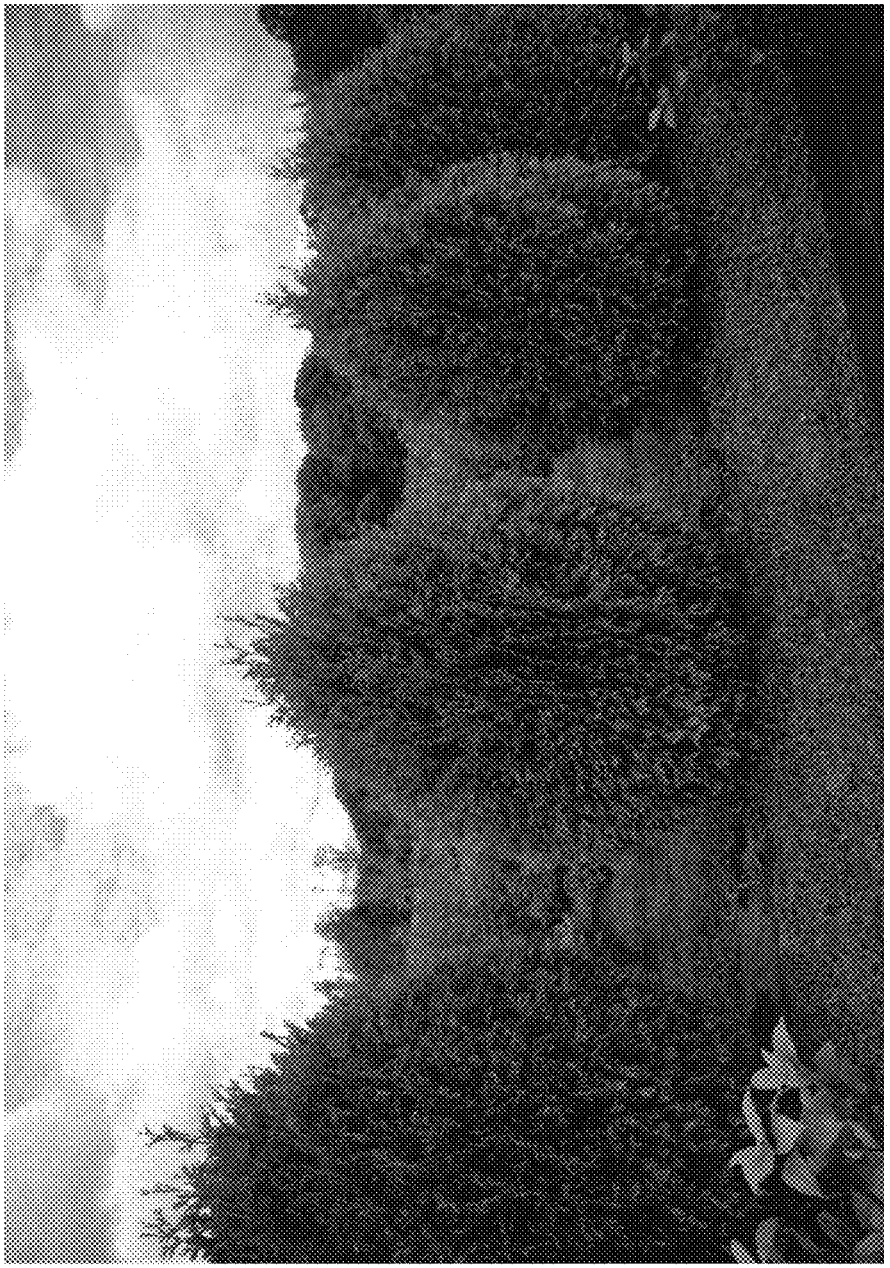

The accompanying photograph in FIG. 1 illustrates in full color typical plants of 'SMNTDGT' grown outdoors in Grand Haven, Mich. The plants are approximately 5 years old, in the ground.

Figure 2:
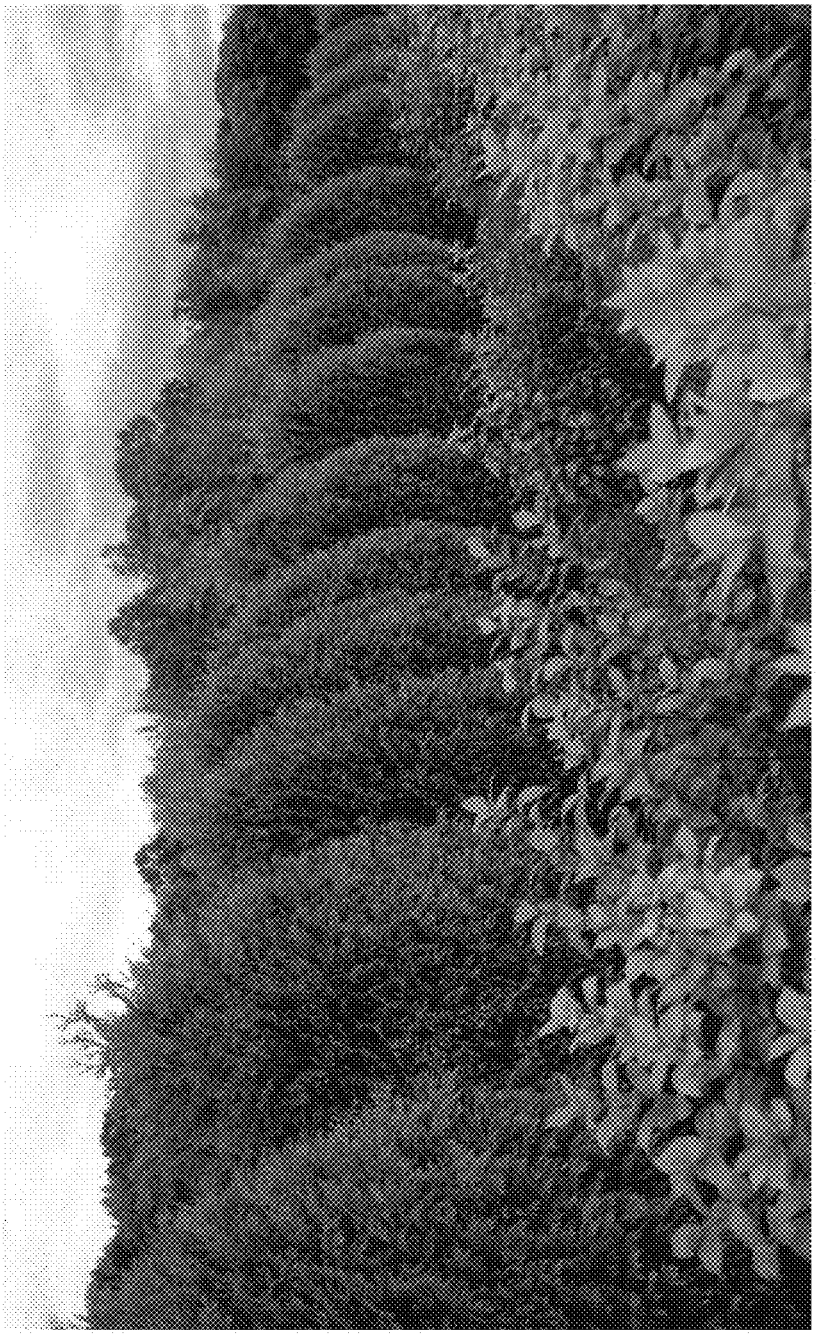

FIG. 2 illustrates another view of a test field of plants of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNTDGT' plants grown outdoors in Grand Haven, Mich. Plants are approximately 1-2 years old, in a 3 gallon nursery container. Measurements and numerical values represent averages of typical plant types.

Botanical classification: *Thuja occidentalis* 'SMNTDGT'.

PROPAGATION

Time to rooting: About 56 days at approximately 18-27° C.

Root description: Moderately dense branching. Slightly woody, both fine and thick roots present. Colored white and tan, not accurately measured with the RHS chart.

PLANT

Growth habit: Perennial evergreen tree with an ovate habit.

Height: 53 cm.

Plant spread: 44 cm.

Typical growth rate: Slow.

Pinching required: No.

Branching characteristics: Outwards and upwards.

Average number of lateral branches: About 10 major lateral branches.

Length of lateral branches: 40 cm.

Diameter of lateral branches: 5 mm.

Lateral branch shape in cross section: Oval.

Lateral branch texture: Rough, scaly.

Branch angle: About 45 to 80 degrees from center.

Lateral branch color: Greyed-Orange 165C with mature bark near Brown N200B.

Lateral branch strength: Very strong.

Internode length: Average range 1.5 to 3 cm.

FOLIAGE

Leaf:

*Arrangement.*—Alternate, overlapping scales.

*Shape.*—Scales.

*Average length.*—1 mm.

*Average width.*—1 mm.

*Apex.*—Acuminate.

*Base.*—Truncate.

*Margin.*—Entire.

*Texture of top surface.*—Smooth, waxy.

*Texture of bottom surface.*—Smooth, waxy.

*Color.*—Young foliage upper side: Yellow-orange 19D, greyed-orange 170C fading into yellow-green 144A. Young foliage under side: Yellow-orange 19D, greyed-orange 170C fading into yellow-green 144A. Mature foliage upper side: Green 143A. Mature foliage under side: Green 143A.

*Venation.*—Indistinguishable from leaf blade.

*Fragrance.*—None.

FLOWER

Flowering not observed.

OTHER CHARACTERISTICS

Disease and pest resistance: Neither resistance nor susceptibility observed.

Drought tolerance: No tolerance for drought.

Temperature tolerance: −29° C. to 39° C.

What is claimed is:

1. A new and distinct cultivar of *Thuja* plant named 'SMNTDGT' as herein illustrated and described.

* * * * *